United States Patent
Lohf et al.

(10) Patent No.: US 7,910,073 B2
(45) Date of Patent: Mar. 22, 2011

(54) MICROFLUIDIC SYSTEM

(75) Inventors: Astrid Lohf, Erlangen (DE); Reinhold Schneeberger, Seukendorf (DE); Waldemar Wenzel, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 415 days.

(21) Appl. No.: 11/992,803

(22) PCT Filed: Sep. 28, 2006

(86) PCT No.: PCT/EP2006/066860
§ 371 (c)(1),
(2), (4) Date: Mar. 28, 2008

(87) PCT Pub. No.: WO2007/036558
PCT Pub. Date: Apr. 5, 2007

(65) Prior Publication Data
US 2009/0126504 A1    May 21, 2009

(30) Foreign Application Priority Data
Sep. 30, 2005 (DE) .......................... 10 2005 047 041

(51) Int. Cl.
*B01L 3/00* (2006.01)
*B01L 3/02* (2006.01)
*B01L 99/00* (2010.01)
*F04B 19/00* (2006.01)
*B01D 5/00* (2006.01)

(52) U.S. Cl. ........ 422/502; 422/503; 422/505; 422/510; 422/517; 422/518; 422/532; 422/537; 422/544; 422/547; 422/554; 422/565; 422/566

(58) Field of Classification Search .................. 422/68.1, 422/81, 82, 99–102; 436/180; 429/99
See application file for complete search history.

(56) References Cited

U.S. PATENT DOCUMENTS
5,273,905 A * 12/1993 Muller et al. .............. 435/286.5
2004/0086424 A1* 5/2004 Schembri ........................ 422/58

FOREIGN PATENT DOCUMENTS
| DE | 694 11 026 T2 | 7/1996 |
| DE | 297 03-788 U1 | 8/1997 |
| DE | 10 2004 022 423 A1 | 12/2005 |
| EP | 1 188 476 A2 | 3/2002 |
| WO | WO 00/03169 A2 | 2/2000 |
| WO | WO 02/065221 A2 | 8/2002 |

OTHER PUBLICATIONS

Berg Van Den AL et al., "Modular Concept for Miniature Chemical Systems", Dechema Monographien, Verlag Chemie, Weinheim, DE, 1995, pp. 109-123, vol. 132, XP 000925640, ISSN: 0070-315X.

* cited by examiner

*Primary Examiner* — Jill Warden
*Assistant Examiner* — Dean Kwak

(57) ABSTRACT

The microfluidic system is constituted of modules that comprise one microfluidic unit and one corresponding electric control unit each and that are retained on a rear panel unit next to each other in a row. To prevent the formation of accumulation of ignitable or toxic gas mixtures a fluid conduit for a rinsing fluid extends through the rear panel unit. Branches lead from said fluid conduit to the modules, and said branches flowing into respective distributor compartments that extend vertically across the module height in the modules. Said distributor compartments are delimited in relation to the interior of the respective module by a distributor panel that is provide with openings. The interior of the respective module comprises, on its lower or rear surface, an exit opening for the rinsing fluid.

16 Claims, 3 Drawing Sheets

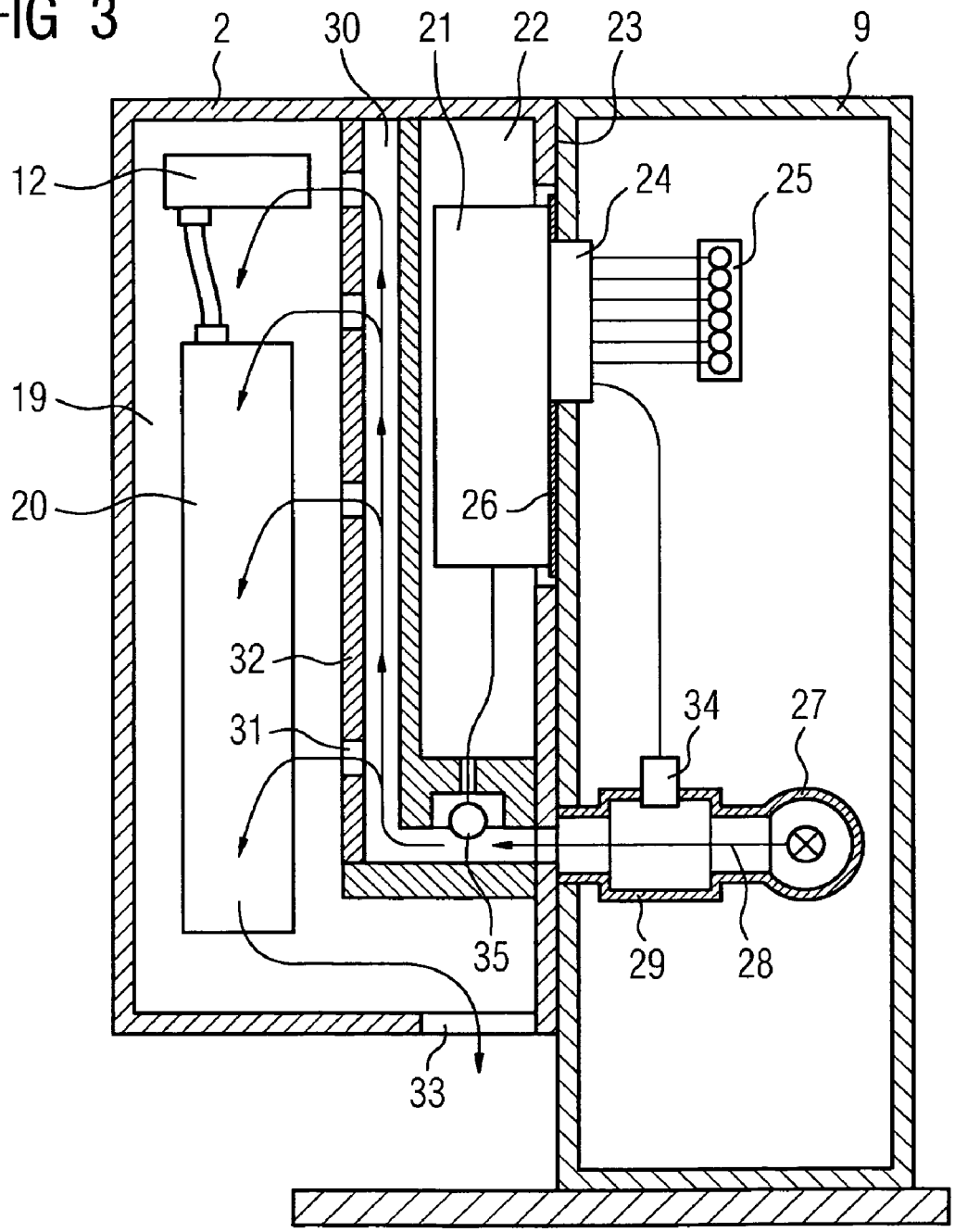

MICROFLUIDIC SYSTEM

CROSS REFERENCE TO RELATED APPLICATIONS

This application is the US National Stage of International Application No. PCT/EP2006/066860, filed Sep. 28, 2006 and claims the benefit thereof. The International Application claims the benefits of German application No. 10 2005 047 041.6 DE filed Sep. 30, 2005, both of the applications are incorporated by reference herein in their entirety.

FIELD OF INVENTION

The invention relates to a microfluidic system, as is likewise known from WO 01/36085 A1, WO 01/73823 A2 and WO 02/065221 A2. The known microfluidic systems consist of several modules, which each comprise a microfluidic unit and an associated electric control unit and can be mounted on their rear faces on a mounting rail in series next to each other. The control units of the different modules are interconnected by way of an electric line bus and the microfluidic units are interconnected by way of a fluid bus. As WO 02/065221 A2 shows, the fluid bus can be formed such that the microfluidic units of adjacent modules in each instance are interconnected via connecting parts that contain connection channels and that span the relevant modules.

BACKGROUND OF INVENTION

A modular microfluidic system also forms the subject matter of the prior German patent application with the official file reference 10 2004 022 423.4.

In the modules of the microfluidic system, toxic or ignitable gas mixtures can form in the event of a leakage, said gas mixtures endangering the system and its users.

SUMMARY OF INVENTION

An object underlying the invention is thus to specify a microfluidic system, in which the formation or accumulation of such gas mixtures is prevented.

According to the invention, the object is achieved by a microfluidic system, which consists of modules arranged in series next to each other, each of which contains a microfluidic unit and an associated electric control unit,
  with the rear faces of the modules lying against a common vertical rear wall unit and being held against said unit,
  with the control units being connectable to an electric line bus that extends through the rear wall unit via electric connector parts arranged on the rear faces of the modules and on the rear wall unit,
  with the microfluidic units of two adjacent modules in each instance being interconnected to allow the passage of fluid via a connecting part that contains connection channels and that spans the relevant modules,
  with a fluid conduit for a rinsing fluid extending through the rear wall unit and branches leading from said fluid conduit to the modules,
  with the branches each flowing into a distributor compartment that extends vertically across the module height in the modules, said distributor compartment being delimited in relation to the interior of the respective module by a distributor panel that is provided with openings, and
  with the interior of the respective module containing an exit opening for the rinsing fluid on its lower or rear surface.

The interior of each module is rinsed with the rinsing fluid, for instance compressed air or nitrogen, via a corresponding branch from the fluid conduit in the rear wall unit. To achieve a uniform flow through the interior of the module here and thus to prevent the formation of dangerous gas mixtures in the dead spots, the rinsing fluid is conveyed in an equally distributed manner over the distributor compartment and the openings in the distributor panel across the module height into the interior of the module. The distributor compartment can be embodied as a slit between the rear wall of the module and the distributor panel for instance. A module-specific distribution of the rinsing fluid in the interior of the module can be set as a function of the module fixtures for instance, using the opening pattern, i.e. number, arrangement and size of the openings in the distributor panel. On this account, the distributor panels are preferably held in the modules in an exchangeable fashion. After flushing the modules, the gas mixture is purged downwards or backwards out of the modules by the user of the microfluidic system and is, if necessary, siphoned off there.

In the modules, the respective control unit can be arranged in a compartment which is shut off in relation to the region rinsed by the rinsing fluid, with the required blast protection being achieved by means of capsulation and the electronic system of the control unit being protected against potentially corrosive fluid mixtures. In this way, the compartment containing the control unit is preferably arranged on the rear face of the module, with the control unit being thermally connected to the rear wall unit and cooled down thereby, if necessary blower-cooled using a cooling fluid conveyed in the rear wall unit, a ventilator or Peltier elements.

To prevent an uncontrolled exit of the rinsing fluid from the rear wall unit, the branches at those positions of the rear wall unit where no modules are retained, can be closed by means of a blank plug or a valve which can be actuated by the module lying against the rear wall. Furthermore, the branches of the rear wall unit preferably have flow rate sensors and/or pressure sensors to monitor the rinsing fluid pressure and/or flow rate (volume flow). It is thus possible on the one hand to identify whether rinsing fluid exits in an uncontrolled manner at a location which is unoccupied by a module or whether the rinsing fluid pressure or flow rate is sufficient in the presence of a module. For this purpose, the flow rate and/or pressure sensors can be connected to a superior controller of the microfluidic system by way of the line bus in the rear wall unit and/or to the control facilities belonging to the module by way of the connector parts.

The modules themselves preferably have flow rate sensors in the path of the rinsing fluid upstream of the distributor compartment in order to monitor the rinsing fluid flow rate, with the flow rate sensors being connected to the control facilities belonging to the module.

BRIEF DESCRIPTION OF THE DRAWINGS

A further explanation of the invention follows in detail below with reference to the figures of the drawings, in which:
FIG. 2 shows the upper part of one of the modules with a microfluidic part and connecting parts and
  FIG. 3 shows a sectional view of one of the modules and the rear wall unit.

DETAILED DESCRIPTION OF INVENTION

Figure 1:
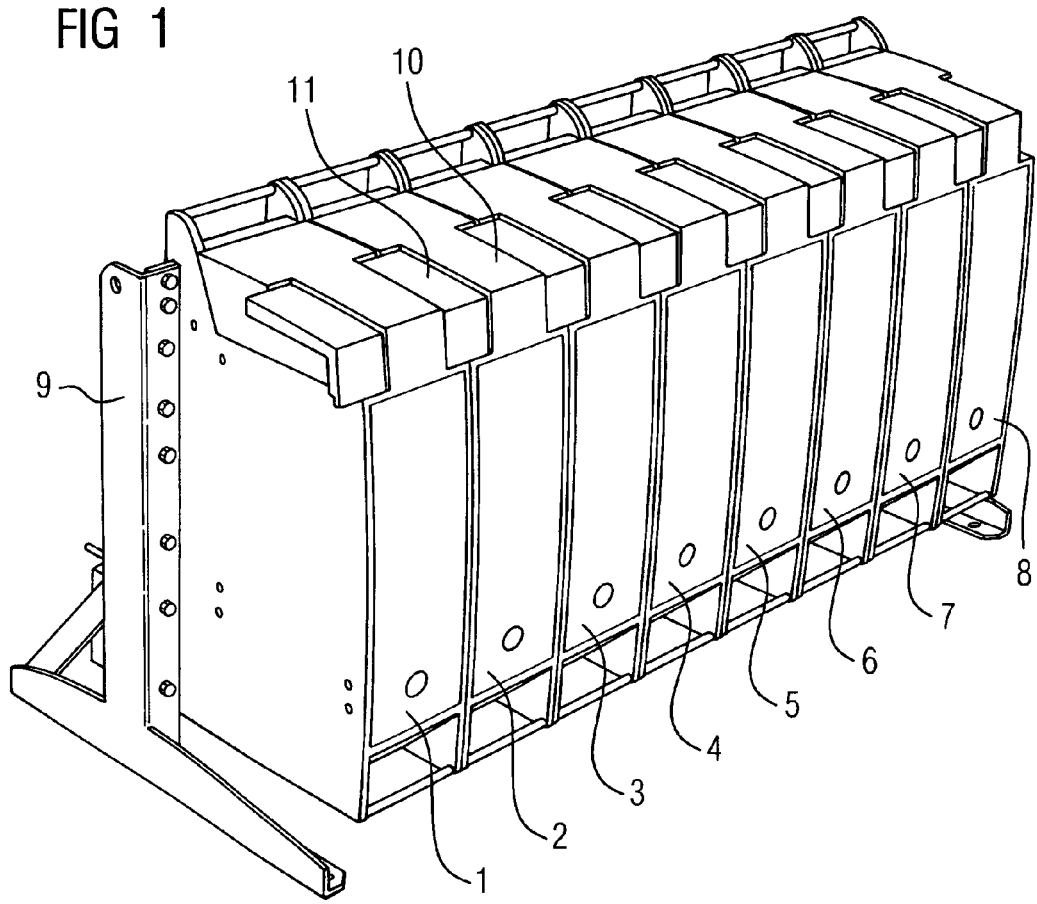
FIG. 1 shows an exemplary embodiment of the modular microfluidic system according to the invention.

FIG. 1 shows a microfluidic system with modules 1 to 8, which are arranged next to each other in series and are retained with their rear faces on a rear wall unit 9 in the form of a mounting frame. In this process, the modules 1 and 8 form the end modules, i.e. the start and end module, of the microfluidic system. Each module 1 and 8 contains a microfluidic part and an associated electric control unit. The control units of the different modules are interconnected by way of an electric line bus and the microfluidic parts are interconnected by way of a fluid bus. The electric line bus extends through the rear wall unit 9, with the modules 1 to 8 being detachably connected to the line bus by way of rear-facing plug connectors. The fluid bus is formed by connecting parts containing connection channels, said connecting parts interconnecting the microfluidic parts of adjacent modules 1 and 8 in each instance to allow the passage of fluid. The microfluidic parts are arranged in the region of the top of the module and are covered during normal operation of the microfluidic system by cover hoods 10 which are retained in a detachable fashion on the modules 1 to 8. The connecting parts connecting the microfluidic parts of adjacent modules 1 to 8 in each instance are covered by additional cover hoods 11.

Figure 2:
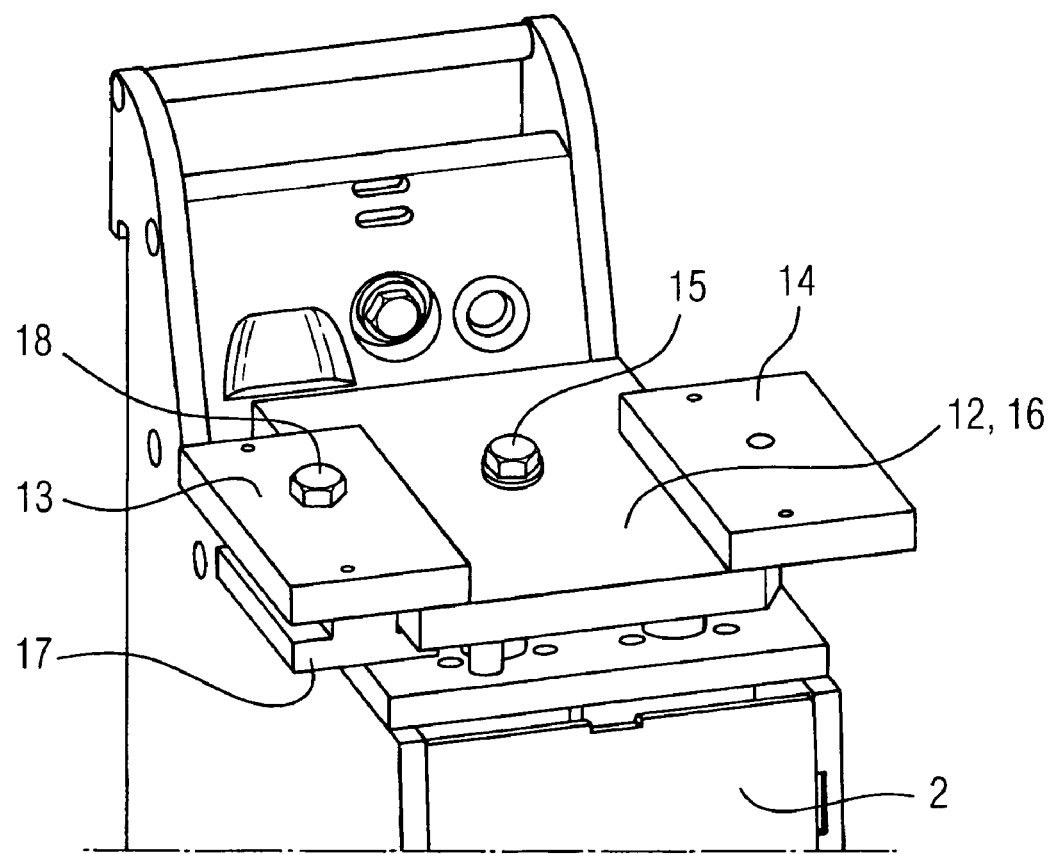

FIG. 2 shows the upper part of one of the modules, e.g. 2, when the cover hoods 10, 11 have been removed, such that the microfluidic part 12 and the connecting parts 13 and 14 can be visible toward the adjacent modules 1 and 3. The panel-shaped microfluidic part 12 lies with its lower surface in a locally delimited region of the panel center on a supporting surface of the module 2 and is pressed against this by means of a screw 15. The microfluidic part 12 contains a fluid channel system with fluid connections, which are arranged on the top 16 of the microfluidic part 12 in the border regions toward the microfluidic parts of the adjacent modules 1 and 3. The fluid connections of two adjacent microfluidic parts in each instance, e.g. the microfluidic part 12 of the module 2 and the corresponding microfluidic part of module 1, are interconnected by the connection channels in the connecting part, e.g. 13, which spans the two microfluidic parts and rests on its top in the border regions. A clamping part 17 is disposed in the opposite border regions on the lower surface of the two adjacent microfluidic parts, said clamping part being connected to the connecting part 13 in the region between the two microfluidic parts by way of an additional screw 18 and pressing this against the top of the two microfluidic parts.

FIG. 3 shows a cross-sectional schematic illustration of the module 2 and the rear wall unit 9. The interior 19 of the module 2 contains the microfluidic part 12 and an additional micro or macrofluidic unit 20, for instance a pump. The control unit 21 is arranged in a rear-facing compartment 22 of the module 2 and is connected to the electric line bus 25 in the rear wall unit 9 by way of a plug connector 24 on the rear face 23 of the module 2. The control unit 21 is therewith flush with the rear wall unit 9 by way of a heat conductive intermediate layer 26 and can thus radiate heat loss onto the rear wall unit 9. The compartment 22 shuts the control unit 21 and plug connector 24 off from the outside, as a result of which the required ignition blast is achieved and the electronic system of the control unit 21 is protected against potentially occurring corrosive fluid mixtures.

A fluid conduit 27 extends through the rear wall unit 9, a pressurized rinsing fluid 28 being introduced into said fluid conduit from the outside, and from which fluid conduit a branch 29 is led to the relevant module 2 at each assembly area for a module, here for module 2. If the area is not occupied with a module, the relevant branch is sealed with a plug. The branch 29 flows into a slit-shaped distributor compartment 30 which extends vertically across the module height in the module 2 between the shut-off compartment 22 for the control unit 21 and a distributor panel 32 that is provided with openings, said distributor panel 32 delimiting the distributor compartment 30 in relation to the interior 19 of the module 2. The rinsing fluid 28 is equally distributed over the distributor compartment 30 and the openings 31 in the distributor panel 32 across the module height into the interior 19 of the module 2 so that the formation or accumulation of dangerous gas mixtures in the interior of the module 18 is prevented in the event of leakages on the fluid units 12 and 20. A module-specific distribution of the rinsing fluid 28 in the interior of the module 19 can be adjusted as a function of the module fixtures 12 and 20 for instance, using the number, arrangement and size of the openings in the distributor panel. After flushing the interior of the module 19, the rinsing fluid 28 and if necessary the gas mixture which has been diluted thereby is siphoned off downwards out of the module 2 through an exit opening 33 by the user of the microfluidic system.

The rear wall unit 9 has a flow rate and/or pressure sensor 34 on the branches, here the branch 29, of the fluid conduit 27 in each instance, which monitors the pressure and/or volume flow of the rinsing fluid and is connected for this to the control device 21 belonging to the module by way of the plug connector 24. The module 2 likewise has a flow rate sensor 35 in the path of the rinsing fluid 28 upstream of the distributor compartment 30 which is connected to the control device 21 and monitors the flow rate of the rinsing fluid 28. Such a flow rate sensor 35 consists in the simplest case of a sail, which protrudes into the path of the rinsing fluid 28 and is deflected by the flow; the deflection is achieved here by means of a photoelectric barrier.

The invention claimed is:

1. A microfluidic system, comprising:
a plurality of modules arranged in series next to each other, wherein each module has a microfluidic unit and an associated electric control unit, and wherein each module has an electric connector on a rear face of the module;
a common vertical rear wall unit, wherein the rear faces of the modules lie against the common vertical rear wall unit and are held against the common vertical rear wall unit;
an electric line bus extending through the rear wall unit, wherein the rear wall unit has electric connectors, wherein the control units are connectable to the electric line bus extending through the rear wall unit via the electric connectors arranged on the rear faces of the modules and on the rear wall unit;
a connecting part with connection channels to span two adjacent modules, wherein the microfluidic units of the two adjacent modules are interconnected via the connection channels to allow a passage of fluid;
a fluid conduit for a rinsing fluid extending through the rear wall unit;
branches leading from the fluid conduit to the modules, wherein the branches each flow into a distributor compartment which extends vertically across the module height in the modules, wherein the distributor compartment is delimited in relation to an interior of the respective module by a distributor panel having openings, wherein the rinsing fluid is equally distributed over the distributor compartment and the openings in the distributor panel across the module height into the interior of the module; and
an exit opening for the rinsing fluid on the lower or rear surface of the module;

wherein the control unit is arranged in the module in a compartment, wherein the compartment is shut off in relation to an area rinsed by the rinsing fluid;

wherein the compartment containing the control unit is on the rear face of the module, and wherein the control unit is thermally connected to the rear wall unit and blower-cooled by the rear wall unit using a ventilator blowing on a cooling fluid or conveyed past a Peltier element in the rear wall unit.

2. The microfluidic system as claimed in claim 1, wherein the branches are closed with a blank plug or a valve, when modules are not present.

3. The microfluidic system as claimed in claim 2, wherein the modules have flow rate sensors for monitoring the rinsing fluid flow rate in the path of a rinsing fluid upstream of the distributor compartment, and wherein the flow rate sensors are connected to the control facilities belonging to the modules.

4. The microfluidic system as claimed in claim 1, wherein the rear wall unit has flow rate sensors on the branches for monitoring the rinsing fluid flow rate.

5. The microfluidic system as claimed in claim 4, wherein the rear wall unit has pressure sensors on the branches for monitoring the rinsing fluid pressure.

6. The microfluidic system as claimed in claim 5, wherein the sensors are connected to a superior controller of the microfluidic system via the line bus in the rear wall unit.

7. The microfluidic system as claimed in claim 4, wherein the sensors are connected to a superior controller of the microfluidic system via the line bus in the rear wall unit.

8. The microfluidic system as claimed in claim 5, wherein the sensors are connected to the electric control unit of the module respectively via the connector parts.

9. The microfluidic system as claimed in claim 8, wherein the modules have flow rate sensors for monitoring the rinsing fluid flow rate in the path of a rinsing fluid upstream of the distributor compartment, and wherein the flow rate sensors are connected to the control facilities belonging to the modules.

10. The microfluidic system as claimed in claim 4, wherein the sensors are connected to the electric control unit of the module respectively via the connector parts.

11. The microfluidic system as claimed in claim 1, wherein the rear wall unit has pressure sensors on the branches for monitoring the rinsing fluid pressure.

12. The microfluidic system as claimed in claim 11, wherein the sensors are connected to a superior controller of the microfluidic system via the line bus in the rear wall unit.

13. The microfluidic system as claimed in claim 11, wherein the sensors are connected to the electric control unit of the module respectively via the connector parts.

14. The microfluidic system as claimed in claim 1, wherein the modules have flow rate sensors for monitoring the rinsing fluid flow rate in the path of a rinsing fluid upstream of the distributor compartment, and wherein the flow rate sensors are connected to the control facilities belonging to the modules.

15. The microfluidic system as claimed in claim 1, wherein the modules have flow rate sensors for monitoring the rinsing fluid flow rate in the path of a rinsing fluid upstream of the distributor compartment, and wherein the flow rate sensors are connected to the control facilities belonging to the modules.

16. The microfluidic system as claimed in claim 1, wherein the modules have flow rate sensors for monitoring the rinsing fluid flow rate in the path of a rinsing fluid upstream of the distributor compartment, and wherein the flow rate sensors are connected to the control facilities belonging to the modules.

* * * * *